(12) United States Patent
Tamoli

(10) Patent No.: US 11,013,778 B2
(45) Date of Patent: May 25, 2021

(54) NICOTINE FREE HERBAL COMPOSITION FOR SMOKING DE-ADDICTION AND TREATMENT OF SIDE-EFFECTS AND/OR AILMENTS FROM SMOKING

(71) Applicant: Gurseet Singh, Mumbai (IN)

(72) Inventor: Sanjay Motilal Tamoli, Mumbai (IN)

(73) Assignee: Singh Gurseet, Mumbai (IN)

( * ) Notice: Subject to any disclaimer, the term of this patent is extended or adjusted under 35 U.S.C. 154(b) by 190 days.

(21) Appl. No.: 16/073,813

(22) PCT Filed: Feb. 22, 2017

(86) PCT No.: PCT/IB2017/050992
§ 371 (c)(1),
(2) Date: Jul. 30, 2018

(87) PCT Pub. No.: WO2017/145056
PCT Pub. Date: Aug. 31, 2017

(65) Prior Publication Data
US 2019/0038700 A1    Feb. 7, 2019

(30) Foreign Application Priority Data
Feb. 23, 2016 (IN) .............................. 201621006288

(51) Int. Cl.
| | |
|---|---|
| A61K 36/906 | (2006.01) |
| A61K 36/48 | (2006.01) |
| A61K 36/00 | (2006.01) |
| A61K 36/81 | (2006.01) |
| A61K 36/9066 | (2006.01) |
| A61K 36/185 | (2006.01) |
| A61K 36/19 | (2006.01) |
| A61K 36/23 | (2006.01) |
| A61K 36/35 | (2006.01) |
| A61K 36/484 | (2006.01) |
| A61K 36/488 | (2006.01) |
| A61K 36/53 | (2006.01) |
| A61K 36/59 | (2006.01) |
| A61K 36/61 | (2006.01) |
| A61K 36/67 | (2006.01) |
| A61K 36/68 | (2006.01) |
| A61K 36/87 | (2006.01) |
| A61K 36/9068 | (2006.01) |

(52) U.S. Cl.
CPC .......... *A61K 36/9066* (2013.01); *A61K 36/00* (2013.01); *A61K 36/185* (2013.01); *A61K 36/19* (2013.01); *A61K 36/23* (2013.01); *A61K 36/35* (2013.01); *A61K 36/48* (2013.01); *A61K 36/484* (2013.01); *A61K 36/488* (2013.01); *A61K 36/53* (2013.01); *A61K 36/59* (2013.01); *A61K 36/61* (2013.01); *A61K 36/67* (2013.01); *A61K 36/68* (2013.01); *A61K 36/81* (2013.01); *A61K 36/87* (2013.01); *A61K 36/9068* (2013.01)

(58) Field of Classification Search
None
See application file for complete search history.

(56) References Cited

U.S. PATENT DOCUMENTS

2006/0137702 A1* 6/2006 Karerat .................. A61K 36/24
                                                                131/352
2011/0014277 A1* 1/2011 Bieley

FOREIGN PATENT DOCUMENTS

WO        WO2006097447        *   9/2006

* cited by examiner

*Primary Examiner* — Michael Barker
*Assistant Examiner* — Randall O Winston
(74) *Attorney, Agent, or Firm* — D'Ambrosio & Menon, PLLC; Usha Menon

(57) ABSTRACT

The present disclosure provides nicotine free anti-smoking compositions comprising synergistic combination of herbal ingredients. In a preferred embodiment of the present disclosure, the anti-smoking composition can include combination of at least two herbs selected from the group consisting of Kapikachu, Ashwagandha, Tulsi, Haridra, Amla, Gokshura, Brahmi, Yashtimadhu, Sunthi, Lavang, Bala, Vidarikand, Jatanamsi, Shatavari, and Musli. In another preferred embodiment of the disclosure, the anti-smoking composition can further include one or more additional herbs selected from the group consisting of Guduchi, Draksha, Sirish, Arjuna, Mandukparni, Vasa, Karpoor, Kankol, Kantakari and Shigru. The formulation(s) in accordance with embodiments of the present disclosure not only provides anti-smoking effect but also treat side-effects and/or ailments arising from smoking.

8 Claims, No Drawings

NICOTINE FREE HERBAL COMPOSITION FOR SMOKING DE-ADDICTION AND TREATMENT OF SIDE-EFFECTS AND/OR AILMENTS FROM SMOKING

FIELD OF THE INVENTION

The present disclosure pertains to technical field of anti-smoking formulation. In particular, the present disclosure pertains to nicotine free composition having synergistic combination of herbs for smoking de-addiction and treatment of side-effects and/or ailments arising from smoking.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Smoking cigarette (ultimately tar, nicotine, ammonia, lead, and cyanide amongst other chemicals) has become major concerns not only for USA (which remains home to large number of smoking addicts) but also for the whole world. During last decade or so, smoking has become passion for all age groups and has not been limited to adults at all. Knowingly or unknowingly smokers invite many diseases and disorders including but not limited to infertility, sterility, giving premature birth to baby during pregnancy, peripheral artery diseases, breathing disorders such as COPD, bronchitis, and emphysema. Smoking almost affects every organ of the body. It causes mouth sores, ulcers and gum disease, causes skin to become dry and lose elasticity, causes stressed heart, sticky blood, fatty deposits, scarred lungs, cilia, belly, lower estrogen levels, erectile dysfunction, high white blood cell count, requiring longer time for wound healing, weakened immune system, tiring of muscles and thinning of bones. Cancer is considered to be the most serious effect caused due to smoking.

There are many options available for the de-addiction of smoking and some of them use nicotine themselves. Nicotine patches, gums, inhalers and sprays are some of the options chosen currently. Some of the quitters also try e-cigarettes that are battery operated devices converting liquid nicotine to vapor. Unlike nicotine replacement therapies, medications available for the de-addiction do not use nicotine but carry serious risks along with them such as causing suicidal behavior, affected vision, unusual dreams and road accidents. Some quitters also choose to go for hypnosis, acupuncture and group counseling.

Considering limitations of the treatment options described in the last paragraph, there is therefore a need in the art to develop a new anti-smoking formulation that is free from the existing drawbacks of the anti-smoking formulations with or without nicotine, having serious side effects such as causing suicidal behavior, unusual dreams, affected vision in the patient. Need is also observed to develop formulation that has synergistic combination of the herbs otherwise used alone. Need is also observed to develop formulation that not only helps in de-addiction of smoking but also treats the ailments and/or side-effects caused by smoking.

To the best of our knowledge, none of the anti-smoking formulations known so far, bring out the combined effect of de-addiction of smoking and treatment of side-effects and/or ailments from smoking such as respiratory diseases like COPD, asthma, chronic bronchitis, cardiovascular diseases like stroke, atherosclerosis, coronary heart disease, peripheral arterial disease, abdominal aortic aneurysm, allergies like cigarette smoke allergy, reproductive effects like ectopic pregnancy, infertility, premature birth to babies etc.

The present invention satisfies the existing needs, as well as others, and generally overcomes the deficiencies found in the prior art.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability.

OBJECTS OF THE INVENTION

It is an object of the present disclosure to provide an anti-smoking composition that does not use nicotine.

Another object of the present disclosure is to provide an anti-smoking composition that uses combination of herbs resulting in synergy.

Another object of the present disclosure is to provide an anti-smoking composition that includes ingredients to treat ailments and/or side-effects caused by smoking.

Yet another object of the present disclosure is to provide an anti-smoking composition that brings out combined effect of de-addiction of smoking and treatment of side-effects and/or ailments caused by smoking.

SUMMARY

As set forth in the detailed description, in accordance with various embodiments of the present disclosure, a nicotine free anti-smoking composition including combination of herbal ingredients is provided.

In a preferred embodiment of the present disclosure, the anti-smoking composition disclosed herein can include combination of at least two herbs selected from the group consisting of Kapikachu, Ashwagandha, Tulsi, Haridra, Amla, Gokshura, Brahmi, Yashtimadhu, Sunthi, Lavang, Bala, Vidarikand, Jatanamsi, Shatavari, and Musli.

In another preferred embodiment of the disclosure, the anti-smoking composition can also include one or more additional herbs selected from the group consisting of Guduchi, Draksha, Sirish, Arjuna, Mandukparni, Vasa, Karpoor, Kankol, Kantakari and Shigru in addition to the combination of at least two herbs selected from the group consisting of Kapikachu, Ashwagandha, Tulsi, Haridra, Amla, Gokshura, Brahmi, Yashtimadhu, Sunthi, Lavang, Bala, Vidarikand, Jatanamsi, Shatavari, and Musli.

The herbs used in the composition according to the embodiments of the present disclosure can show synergism when used in combination with each other. Formulations in accordance with embodiments of the present disclosure can not only provide the desired anti-smoking effect but also treat side-effects and/or ailments arising due to smoking.

Various objects, features, aspects and advantages of the inventive subject matter will become more apparent from the following detailed description of preferred embodiments.

DETAILED DESCRIPTION OF THE INVENTION

The following is a detailed description of embodiments of the present invention. The embodiments are in such detail as to clearly communicate the invention. However, the amount of detail offered is not intended to limit the anticipated variations of embodiments; on the contrary, the intention is to cover all modifications, equivalents, and alternatives falling within the spirit and scope of the present invention as defined by the appended claims.

Each of the appended claims defines a separate invention, which for infringement purposes is recognized as including equivalents to the various elements or limitations specified in the claims. Depending on the context, all references below to the "invention" may in some cases refer to certain specific embodiments only. In other cases it will be recognized that references to the "invention" will refer to subject matter recited in one or more, but not necessarily all, of the claims.

Unless the context requires otherwise, throughout the specification which follow, the word "comprise" and variations thereof, such as, "comprises" and "comprising" are to be construed in an open, inclusive sense that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

In some embodiments, the numbers expressing quantities of ingredients, properties such as concentration, and so forth, used to describe and claim certain embodiments of the invention are to be understood as being modified in some instances by the term "about." Accordingly, in some embodiments, the numerical parameters set forth in the written description are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable.

The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Various terms as used herein are shown below. To the extent a term used in a claim is not defined below, it should be given the broadest definition persons in the pertinent art have given that term as reflected in printed publications and issued patents at the time of filing.

The headings and abstract of the invention provided herein are for convenience only and do not interpret the scope or meaning of the embodiments. Reference will now be made in detail to the exemplary embodiments of the present invention.

Various embodiments of the present disclosure provide nicotine free anti-smoking compositions comprising combination of herbal ingredients. In a preferred embodiment of the present disclosure, the anti-smoking composition can include combination of at least two herbs selected from the group consisting of Kapikachu, Ashwagandha, Tulsi, Haridra, Amla, Gokshura, Brahmi, Yashtimadhu, Sunthi, Lavang, Bala, Vidarikand, Jatanamsi, Shatavari, and Musli.

In some embodiments, the disclosed herbal anti-smoking composition can include a mixture of Kapikachu, Ashwagandha, Tulsi, Haridra, Amla, Gokshura, Brahmi, Yashtimadhu, Sunthi, Lavang, Bala, Vidarikand, Jatanamsi, Shatavari, and Musli.

The herbs in the composition of the present disclosure can have any weight ratio suitable for providing the composition with anti-smoking properties. In one embodiment, same amount of each herb can be used in the composition of the present disclosure.

In certain preferred embodiments, the disclosed herbal anti-smoking composition can include, by weight: 1 to 99% Kapikachu, 1 to 99% Ashwagandha, 1 to 99% Tulsi, 1 to 99% Haridra, 1 to 99% Amla, 1 to 99% Gokshura, 1 to 99% Brahmi, 1 to 99% Yashtimadhu, 1 to 99% Sunthi, 1 to 99% Lavang, 1 to 99% Bala, 1 to 99% Vidarikand, 1 to 99% Jatanamsi, 1 to 99% Shatavari, and 1 to 99% Musli.

In a preferred embodiment of the disclosure, the anti-smoking composition can include one or more additional herbs selected from the group consisting of Guduchi, Draksha, Sirish, Arjuna, Mandukparni, Vasa, Karpoor, Kankol, Kantakari and Shigru.

According to embodiments of the present disclosure, the one or more additional herbs can present in the composition in an amount ranging from 1 to 99% by weight based on total weight of the herbal composition.

Herbs used in the formulations according to the embodiments of the present disclosure show synergism when used in combination with each other. Formulations provided by the embodiments of the present disclosure can treat the ailments and/or side-effects caused by the effects of smoking.

In an embodiment, the herbal formulation disclosed herein may be formulated with one or more pharmaceutically acceptable additives in a suitable dosage form using methods known in the art.

In certain embodiments, the herbal composition of the present disclosure may be orally administered to individuals who try to reduce or quit smoking. For oral administration, the herbal composition may be in the form of dry powder, tablet, lozenges, capsules, aqueous solutions, suspensions, emulsions and syrups.

In one embodiment, the dosage of the herbal formulation can range from 0.01 mg/kg to 50 mg/kg of an individual's body weight per dose. The dosage can be a daily dosage and administered once or twice daily, preferably once daily.

Now herbs used in the formulations of the present disclosure will be described in detail. Following described herbs are exemplary and are not an exhaustive list of herbs that can be used for the purpose of the disclosure.

*Mucuna pruriens* (Kapikachu), native to Africa and tropical Asia, is a tropical legume. Its seeds contain L-DOPA, with trace amounts of serotonin, dimethyltryptamine-n-oxide, bufotenine, 5-MeO-DMT-n-oxide, and beta-carboline. Its leaves contain L-DOPA, dimethyltryptamine, 5-MeO-DMT and dimethyltryptamine-n-oxide. It improves dopamine secretion, levels of adrenaline and nor-adrenaline and has anti-depressant, anti-oxidant and neuro-protective properties.

*Withania somnifera* (Ashwagandha) is normally cultivated in India, Nepal, China and Yemen. Its main chemical constituents are alkaloids and steroidal lactones including tropine and cuscohygrine. The leaves contain the steroidal lactones, withanolides, notably withaferin A. It possesses adaptogenic, anti-stress and anti-oxidant properties.

*Ocimum sanctum* (Tulsi) is cultivated normally in India and Nepal. Its main chemical constituents are oleanolic acid, ursolic acid, rosmarinic acid, eugenol, carvacrol, linalool, β-caryophyllene, β-elemene, and germacrene D. It has anti-allergic, anti-inflammatory, anti-oxidant properties. It also acts as a bronchodilator.

*Curcuma longa* (Turmeric or Haridra) is native to India and its main constituents are a group of compounds called curcuminoids, which include curcumin (diferuloylmethane), demethoxycurcumin, and bisdemethoxycurcumin. It is an immuno-modulator and has anti-carcinogenic, anti-allergic, anti-oxidant properties.

*Emblica officinalis* (Amla) is considered to be sacred by Hindus and has ascorbic acid (vitamin C), ellagitannins such as emblicanin A, emblicanin B, punigluconin and pedunculagin, punicafolin, phyllanemblinin A, phyllanemblin and other polyphenols as its main constituents. It acts as an immuno-stimulant and possesses anti-oxidant properties.

*Tribulus terrestris* (Gokshura) is widely naturalized in America and South Australia and its main constituents are harmane and norharmane. It improves the levels of adrenaline and nor-adrenaline and possesses diuretic and anti-oxidant properties.

*Bacopa monnieri* (Brahmi) is named after the creator god of the Hindu pantheon i.e. Brahma. Its main constituents are bacosides, brahmine, nicotine, herpestine, D-mannitol, apigenin, hersaponin, monnierasides cucurbitacin and plantainoside B. It acts as a relaxant, brain tonic and stress reliever.

*Glycyrrhiza glabra* (Yashtimadhu) is a herbaceous perennial legume native to southern Europe, India, and parts of Asia. Its main constituents are anethole, glycyrrhizin, glabrene and glabridin. It imparts sweet taste to the product. It acts as a mucolytic, excellent respiratory tonic and has anti-oxidant and anti-allergic properties.

*Zingiber officinale* (Sunthi) is native to Southern Asia. Its main constituents are zingerone, shogaols, and gingerols, and volatile oils. It enhances bioavailability, therapeutic efficacy and helps in faster absorption. It improves gastrointestinal health.

Clove (Lavang) is native to Indonesia. Its main constituents are Eugenol, acetyl eugenol, beta-caryophyllene and vanillin, crategolic acid, tannins, flavonoids, triterpenoids, and triterpenoids. It possesses anti-allergic and anti-inflammatory properties. It protects against ciliary damage and acts as a bronchodilator.

*Sida cordifolia* (Bala) is native to India. Its main constituents are β-phenethylamine, ephedrine, pseudo-ephedrine, S-(+)-Nb-methyltryptophan methyl ester, hypaphorine, vasicinone, vasicinol, choline, and betaine. It acts as an antipyretic, astringent, diuretic, and tonic. It is useful in treatment of bronchial asthma, tuberculosis, colds, flu, swine flu, chills, lack of perspiration, headaches, nasal congestion, cough and wheezing, urinary infections, sore mouth, and fluid retention. It is also used for heart disease, stroke, facial paralysis, tissue pain and swelling (inflammation), sciatic nerve pain, insanity, nerve pain, nerve inflammation, ongoing achy joints (chronic rheumatism), and unwanted weight loss.

*Pueraria tuberosa* (Vidarikand) is native to India, Pakistan, and Nepal. Its main constituents are puerarin, diadzein, daidzin, â-sitosterol and sigmasterols. It is useful as an immuno-stimulant, enhancer of sperm count and sperm motility, and a diuretic. It reduces dryness of body, relieves constipation and cures skin diseases causing discoloration. It exhibits good hypoglycemic, expectorant, cardiotonic, antipyretic, anti-inflammatory and anti-oxidant properties. It is beneficial in conditions of male and female infertility.

*Nardostachys jatamansi* (Jatanamsi) is native to eastern Himalayas. Its main constituents are acaciin, ursolie acid, octacosanol, kanshone A, nardosinonediol, nardosinone, aristolen-9beta-ol, oleanolic acid, and beta-sitosterol. It is hepatoprotective, analgesic, diuretic and relieves headache, stress and migraine. It is a cardio-tonic, neuro-tonic, and anti-depressant. It is used to treat insomnia and birth related problems.

*Asparagus racemosus* (Shatavari) is common throughout Nepal, Sri Lanka, India and the Himalayas. Its main constituents are Asparagamine A, a polycyclic alkaloid, shatavaroside A, shatavaroside B, filiasparoside C, shatavarins and 8-methoxy-5,6,4'-trihydroxyisoflavone 7-O-beta-D-glucopyranoside. It has anti-oxidant, antibacterial and immuno-stimulant properties. It is a reproductive tonic, demulcent for the digestive system, and a powerful adaptogen. It is useful for upset stomach (dyspepsia), constipation, stomach spasms, and stomach ulcers. It is also used for fluid retention, pain, anxiety, cancer, diarrhea, bronchitis, tuberculosis, dementia, and diabetes.

*Asparagus adscendens* (Musli) finds use in the treatment of infections. Its main constituents are asparagin and stigmasterol. It is useful in the management of diabetes, gallbladder/kidney stones, constipation, anemia, dry sores, nerve pain, neuritis, parasitic illness, and cancer etc. It is a rejuvenation remedy.

*Tinospora cordifolia* (Guduchi) is indigenous to India, Myanmar and Sri Lanka. Its main constituents are Columbin, tinosporaside, jatrorhizine, palmatine, berberine, tembeterine, tinocordifolioside, phenylpropene disaccharides, choline, tinosporic acid, tinosporal, and tinosporon. It is useful forjaundice, diabetes, high cholesterol, allergic rhinitis, upset stomach, gout, lymphoma and other cancers, rheumatoid arthritis, hepatitis, peptic ulcer disease, and to boost the immune system. It also has anti-oxidant properties.

*Vitis vinefera* (Draksha) has Phenolics, Stilbenoids, and Anthocyanins as main constituents. It is venotonic, vaso protective, astringent and a diuretic. It has anti-oxidant, anti-inflammatory, vitaminic, tonic, anticancer and hepato protective properties.

*Albizzia lebbeck* (Sirish) is native to Indomalaya, New Guinea and Northern Australia. Its main use is as anti-poisoning herb. It specifically acts on the respiratory tract as an anti-inflammatory and protects against damage due to allergic factors.

*Terminalia arjuna* (Arjuna) is usually found in Bangladesh and India. Its main constituents are calcium carbonate, other calcium salts, tanninaluminium, magnesium, organic acid, colouring matter and sugar. Other active constituents include tannins, triterpenoid saponins, flavonoids, Gallic acid, ellagic acid, oligomeric proanthocyanidins (OPCs), phytosterols, zinc, and copper. It is useful in the treatment of cancer and cardiovascular disorders. It possesses hepato protective, cholesterol-reducing, and anti-oxidant properties.

*Centella asiatica* (Mandukparni) is native to Asia. Its main constituents include asiaticoside, brahmoside, asiatic acid, and brahmic acid also known as madecassic acid. Other constituents include centellose, centelloside, and madecassoside. It has neuro protective, hepato protective, anti-cancer, anti-anxiety and wound-healing properties.

*Adhatoda vasica* (Vasa) is commonly found throughout Sri Lanka, Nepal, India, Pakistan, Indonesia, Malaysia, and China, as well as Panama. Its main constituents include alkaloids mainly vasicine, tannins, saponins, phenolics and flavonoids. It is used to relieve cough, cold, whooping-cough, asthma, bronchitis, skin ailments, bleeding gums, pyorrhea. It acts as an expectorant to relieve congestion and dyspnoea.

Camphor (Karpoor) is biosynthesized from geranyl pyrophosphate and shows anesthetic, antimicrobial, cough suppressant, decongestant properties. It is useful in the treatment of respiratory tract diseases, cardiovascular diseases and acts as an analgesic.

*Piper cubeba* (Kankol) finds its mention in the Ayurveda for treatment of oral and dental diseases, loss of voice, halitosis, fevers, and cough amongst others. Its main constituents are monoterpenes and sesquiterpenes, the oxides 1,4- and 1,8-cineole and cubebol. It acts as a diuretic. It possesses anti-inflammatory properties. It relieves cough and asthmatic conditions.

*Solanum xanthocarpum* (Kantakari) is native to Asia. Its main uses are for finger abscess, cough, asthma and chest pain. It possesses anti-bacterial benefits. It relieves bronchial asthma, bronchitis and chronic cough.

*Moringa oleifera* (Shigru) is native to India. Its immature seed pods are known as 'drumsticks' and are popular as food variety. It possesses anti-diabetic, anti-oxidant, anti-inflammatory, cholesterol-lowering properties. It protects against some of the effects of arsenic toxicity.

All herbs that either show anti-smoking property or treat the side-effects and/or ailments arising from smoking, either on its own or when combined with herbs used according to embodiments of the disclosure fall within the scope of this invention.

While the foregoing description discloses various embodiments of the disclosure, other and further embodiments of the invention may be devised without departing from the basic scope of the disclosure. The invention is not limited to the described embodiments, versions or examples, which are included to enable a person having ordinary skill in the art to make and use the invention when combined with information and knowledge available to the person having ordinary skill in the art.

Advantages of the Invention

The present disclosure provides an anti-smoking composition that does not use nicotine.

The present disclosure provides an anti-smoking composition that uses combination of herbs resulting in synergy.

The present disclosure provides an anti-smoking composition that has ingredients to treat ailments and/or side-effects caused by cigarette/beedi smoking.

The present disclosure provides an anti-smoking composition that brings out combined effect of de-addiction of tobacco smoking and treatment of side-effects and/or ailments caused by tobacco smoking.

The present disclosure provides an anti-smoking composition that improves the quality of life of tobacco smokers both in terms of physical and psychological health.

The present disclosure provides an anti-smoking composition that can improve the capacity of lungs of tobacco smokers.

The present disclosure provides an anti-smoking composition that can reduce stress to smokers resulting from tobacco smoke.

The present disclosure provides an anti-smoking composition that can help smokers quit or reduce smoking cigarettes/beedi.

The present disclosure provides an anti-smoking composition that can decrease the levels of carbon monoxide (CO) and carboxyhemoglobin (COHb) in tobacco smokers.

The present disclosure provides an anti-smoking composition that can reduce the risk of cardiovascular disorders in cigarette/beedi smokers.

The present disclosure provides an anti-smoking composition that can increase tobacco smoker's energy level, stamina and physical strength.

The present disclosure provides an anti-smoking composition that can contribute to expansion of tobacco smoker's chest.

The present disclosure provides an anti-smoking composition that can increase total Testosterone level in cigarette/beedi smokers.

I claim:

1. A herbal composition for promoting smoking cessation in an individual with a nicotine addiction, the composition comprising:
    Kapikachu (*Mucuna pruriens*) in an amount ranging from 15% to 35% by weight of the composition;
    Ashwagandha (*Withania somnifera*) in an amount ranging from 5% to 15% by weight of the composition;
    at least one herb selected from the group consisting of Tulsi, Vasa, Haridra, Amla, Gokshura, Brahmi, Yashtimadhu, Sunthi, Lavang, Bala, Vidarikand, Jatamansi, Shatavari and Mush; and
    optionally, one or more pharmaceutically acceptable additives.

2. The herbal composition as claimed in claim 1, further comprising one or more additional herbs selected from the group consisting of Guduchi, Draksha, Sirish, Arjuna, Mandukparni, Kapoor, Kankol, Kantakari and Shigu.

3. The herbal composition as claimed in claim 1, wherein the composition comprises Kapikachu, Ashwagandha, Tulsi, Haridra, Amla, Gokshura, Brahmi, Yashtimadhu, Sirish, Sunthi, Lavang, and optionally one or more pharmaceutically acceptable additives.

4. The herbal composition as claimed in claim 3, wherein the composition comprises, by weight of the herbal composition:

15% to 35% Kapikachu,
5% to 15% Ashwagandha,
2.5% to 7.5% Tulsi,
2.5% to 7.5% Haridra,
2.5% to 7.5% Amla,
2.5% to 7.5% Gokshura,
2.5% to 7.5% Brahmi,
5% to 15% Yashtimadhu,
1% to 4% Sirish,
1% to 4% Sunthi,
0.5% to 3% Lavang,
and 0% to 40% one or more pharmaceutically acceptable additives.

5. The herbal composition as claimed in claim 1, wherein the composition is a solid composition.

6. The herbal composition as claimed in claim 1, wherein the composition is nicotine free.

7. The herbal composition as claimed in claim 1, wherein the composition is in a form of dry powder, tablet, lozenge, capsule, aqueous solution, suspension, emulsion or syrup.

8. The herbal composition as claimed in claim 1, wherein the composition is used for treatment of side-effects and/or ailments from smoking.

\* \* \* \* \*